(12) United States Patent
Mang et al.

(10) Patent No.: US 8,180,423 B2
(45) Date of Patent: May 15, 2012

(54) SENSOR WITH INCREASED BIOCOMPATIBILITY

(75) Inventors: Andre Mang, Grenzach-Whylen (DE); Harvey B. Buck, Jr., Indianapolis, IN (US); Michael D. Garrison, Sparta, NJ (US); Walter Jernigan, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1696 days.

(21) Appl. No.: 11/392,134

(22) Filed: Mar. 29, 2006

(65) Prior Publication Data

US 2007/0007133 A1    Jan. 11, 2007

Related U.S. Application Data

(63) Continuation of application No. PCT/US04/32293, filed on Sep. 30, 2004.

(60) Provisional application No. 60/542,953, filed on Feb. 9, 2004, provisional application No. 60/507,426, filed on Sep. 30, 2003, provisional application No. 60/507,426, filed on Sep. 30, 2003.

(51) Int. Cl.
*A61B 5/05* (2006.01)
(52) U.S. Cl. ............ 600/345
(58) Field of Classification Search ............ 600/345, 600/347, 365; 204/403.01
See application file for complete search history.

(56) References Cited

U.S. PATENT DOCUMENTS

| | | | |
|---|---|---|---|
| 4,650,547 A | 3/1987 | Gough | |
| 5,063,081 A * | 11/1991 | Cozzette et al. | 435/4 |
| 5,385,846 A | 1/1995 | Ochs | |
| 5,403,462 A * | 4/1995 | Lev et al. | 204/403.15 |
| 5,497,772 A * | 3/1996 | Schulman et al. | 600/347 |
| 5,916,156 A | 6/1999 | Hildenbrand | |
| 6,144,869 A * | 11/2000 | Berner et al. | 600/347 |
| 6,175,752 B1 * | 1/2001 | Say et al. | 600/345 |
| 6,343,225 B1 | 1/2002 | Clark | |
| 2001/0051768 A1 | 12/2001 | Schulman | |

FOREIGN PATENT DOCUMENTS

| | | |
|---|---|---|
| EP | 1113263 | 7/2001 |
| WO | WO 01/69222 | 9/2001 |

* cited by examiner

*Primary Examiner* — Patricia Mallari
(74) *Attorney, Agent, or Firm* — Woodard Emhardt Moriarty McNett & Henry LLP

(57) ABSTRACT

Sensors and methods for producing them are disclosed. A cavity is created and filled with a reagent that includes a conductive matrix, enzyme, catalyst, and binding agent, in a preferred embodiment. The cavity is substantially enclosed, leaving enough of an opening to allow the sample to enter. A portion of the material surrounding the cavity is preferably permeable to a substance useful for measuring reaction, but not to the reagent or the sample. Cavities that have the shape of a cone, conical frustum, pyramidal frustum, and right circular cylinder are given as examples. Other systems include a membrane that contains the sensor's active area and defines an internal volume of fluid, where the membrane or internal volume has a particular geometric relationship to the active area.

17 Claims, 6 Drawing Sheets

SENSOR WITH INCREASED BIOCOMPATIBILITY

CROSS-REFERENCE TO RELATED APPLICATION

This application is a continuation of International Application No. PCT/US04/32293 filed Sep. 30, 2004, which claims the benefit of U.S. Provisional Application No. 60/507,399 filed Sep. 30, 2003, U.S. Provisional Application No. 60/507,426 filed Sep. 30, 2003, and U.S. Provisional Application No. 60/542,953 filed Feb. 9, 2004.

BACKGROUND

The present invention relates to in vivo measurement. More specifically, the present invention relates to sensing, and sensors for sensing, the concentration of particular substances in bodily fluids.

Measurement of the concentration of particular chemicals in bodily fluids is useful for many types of medical diagnosis and treatment. Insulin-dependent diabetic patients, for example, might measure the concentration of glucose in their blood multiple times per day. In vivo sensors have been developed and are useful in some situations for repeated or continuous testing, but are limited in durability, accuracy, ease of manufacture, and potential lifetime in use. There is thus a need for improved in vivo sensors and sensing techniques.

Some sensors have been developed that limit a reaction between analyte and reagent by using membranes to control the flow of analyte therethrough. Using these membranes adds to the design cost, manufacturing cost, and difficulty in use of such sensors. There is thus a further need for improved in vivo sensors and sensing techniques.

SUMMARY

It is thus an object of various embodiments of the present invention to provide sensors and techniques for sensing with improved characteristics of cost, accuracy, simplicity, durability, and in vivo lifetime.

These objects and others are achieved in some embodiments of the present invention by limiting the flow of the sample to or into the electrode using the geometric configuration of the sensor, for example, by providing a small opening into a three-dimensional cavity containing a conductive matrix including a reagent.

One embodiment of the present invention is an electrode for use in vivo to electrochemically detect or measure particular compounds. A first (substrate) layer has, at or adjacent to one end, a contact that is adapted for electrical connection to a meter. That layer and a second layer, the top surface of which is substantially adjacent the bottom surface of the first layer, together define a cavity with an opening through the top surface of the first layer, the opening being spaced apart from the first end of the first layer. A reagent fills at least 20 percent of the cavity, comprises a conductive matrix, and is electrically connected to the contact. In some variations of this embodiment, the first layer is polyimide, and in others the first layer has a thickness between about two mil and about ten mil, or about 50 μm and about 250 μm.

In still other variations of this embodiment, the cavity has a particular relationship with the opening through the top surface of the first layer. For example, in some variations, each cross-section of the cavity taken parallel to the opening, but above the reagent-filled portion, has an area no smaller than the area of the opening. In others, cross-sections of the cavity that intersect the reagent-filled portion also have an area at least as large as the opening. In refinements of this variation, the area of these cross-sections monotonically increases as they are taken farther from the opening. In other variations of this embodiment, either the volume of the electrode or the volume of the containment cavity has a particular numeric relationship with the area of the opening.

Another form of the present invention is a strip for testing the concentration or presence of an analyte that includes a first layer with a top and bottom surface, a contact end and a sensing end, two contacts at or near the contact end, an electrode location at or near the sensing end, another electrode location near the first electrode location, and a cavity within and defined by the main layer at the first electrode location. The cavity has an opening through the top surface, and is at least about twenty percent filled by a conductive matrix comprising a reagent. A conductor electrically connects the cavity and one of the contacts, while another conductor electrically connects the other electrode location and the second contact. A reference electrode is positioned at the second electrode location.

In variations of this embodiment, the cavity is substantially surrounded, except at the opening, by one or more materials that are non-permeable by the analyte. In a refinement of this embodiment, at least one of these materials is permeable to a cofactor of the reagent contained in the cavity. This may be for example oxygen in the case of a glucose sensor in which the reagent comprises glucose oxidase. In some of these variations, one or more of the cofactor-permeable materials form a second layer with one side disposed adjacent to the bottom surface of the main layer.

In other variations in this embodiment, at least a portion of the cavity is defined by a material that is cofactor-permeable. That material may be adjacent to the bottom surface of the first layer. In other variations, the conductive matrix fills at least about eighty percent of the cavity's volume.

In yet other variations on this embodiment, the conductor that reaches the cavity extends into the cavity to at least partially define it. In others, the conductor is disposed along the top surface, while in yet others, the conductor is disposed along the bottom surface of the main layer. In still other variations, the conductive matrix substantially fills the cavity.

In another embodiment of the present invention, an electrochemical sensor includes a substrate, a reference electrode on the substrate, and a working electrode that substantially fills a cavity that is substantially defined by the substrate. The working electrode includes a conducting matrix and an enzyme. In a variation of this embodiment, the conducting matrix comprises carbon particles, and in others, the enzyme is glucose oxidase. In still other variations of this embodiment, the working electrode also includes a catalyst, such as manganese dioxide. In yet other variations, the electrode also includes a binding agent, such as a polymer, and may further include a catalyst, such as manganese dioxide. The binder in some of these variants is a polymer.

In variations of this embodiment, the cavity has a substantially cylindrical shape, while in others it has substantially the shape of a pyramidal frustum or conical frustum. In some of the latter variations, the cavity has a smaller circular surface that is open sufficiently to allow analyte to pass into the cavity, and a larger circular surface that is adjacent an oxygen-permeable material. In yet further variations of this embodiment, one surface of the working electrode is open such that a sample can enter into the electrode without the sample passing through a layer that limits diffusion of the analyte.

DESCRIPTION

Figure 1:
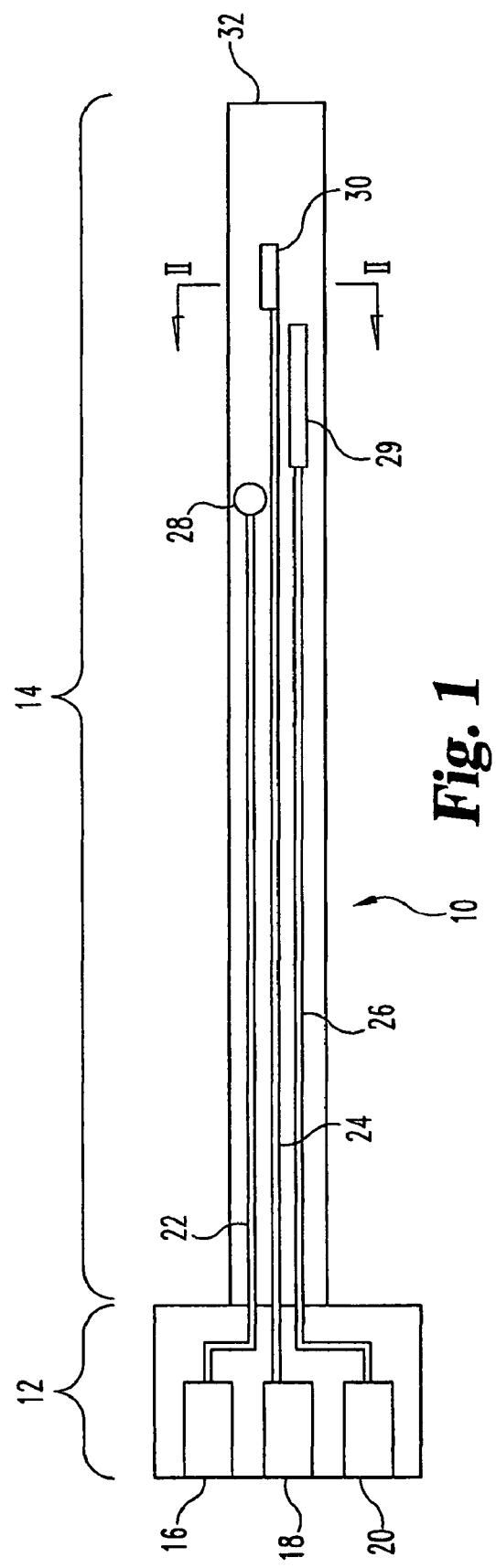
FIG. 1 is a plan view of the substrate layer of a sensor according to one embodiment of the present invention.

For the purpose of promoting an understanding of the principles of the present invention, reference will now be made to the embodiment illustrated in the drawings and specific language will be used to describe the same. It will, nevertheless, be understood that no limitation of the scope of the invention is thereby intended. Any alterations and further modifications of the described or illustrated embodiments, and any further applications of the principles of the invention as illustrated therein, are contemplated as would normally occur to one skilled in the art to which the invention relates.

Various embodiments of the present invention provide an analyte sensor that utilizes the geometry of the sensor to provide an advantageous control of the disposition of analyte and interferants at the sensor's "active area," which herein refers (1) when a substantially planar electrode is used, to the substantially planar region in which analyte reaction and electrochemical detection take place, and (2) when a porous, conductive reagent matrix is used, to the substantially planar area of the opening connecting the volume containing the porous, conducting matrix to the volume of the bodily fluid. The sensor is implanted beneath the skin, and includes a portion that is in contact with the surrounding body fluid, which contains the analyte to be measured. In general, the sensor includes a porous, conductive matrix that has one surface in contact with the body fluid, and a second surface in contact with the surface of a conductive trace that communicates back to a meter operable to assess the analyte based on the electrical signal received from the sensor. The operational area of the porous reagent is significantly larger than the fluid-contacting surface or the surface of the conductive trace, thereby providing greater surface area for reaction of analyte and the electrochemical detection reaction, and for the capture of toxic byproducts of the measured reaction at the electrodes, especially compared to a more planar design.

In a particular embodiment, the volume occupied by the conductive matrix generally increases in cross-sectional area as one proceeds away from the fluid-contacting surface toward the conductive trace surface. In others having partially filled cavities, the cavity generally increases in cross-sectional area as one proceeds away from the fluid-contacting opening down to the volume of reagent. In still others, the cavity generally increases in cross-sectional area as one proceeds away from the fluid-contacting surface.

In some embodiments, a certain volume is opened through the substrate, and reagent is placed therein. A membrane over one opening to the cavity is permeable to the analyte, but not to certain interferants. Another membrane covers the other opening, and is non-permeable to the analyte. In variations of this embodiment, the second membrane is selectively permeable to exclude the analyte, but allow passage of one or more cofactors (such as oxygen) in the fluid to pass into the reaction cavity.

Some embodiments of the present invention are useful for the subcutaneous detection of a wide variety of analytes measurable by electrochemical means. For purposes of example, the discussion herein is provided with reference to a glucose sensor, and commensurate chemistries and other components are identified. However, it will be appreciated by those skilled in the art that other analytes may be readily detected using the present invention, with corresponding changes in the chemistries and the like as are well known in the art.

Referring in particular to the figures, FIG. 1 shows the components of a sensor according to one embodiment of the present invention. Sensor strip 10 has head portion 12 and body portion 14. Head portion 12 includes contacts 16, 18, and 20, for electrical connection to a volt meter, a potentiostat, an ammeter, and/or other detection or display components. The contacts may be directly or indirectly connected with such devices which operate to control the potential or current in the sensor, and to receive and evaluate the electrical signal from the sensing portion of the sensor, as is well known in the art of electrochemical biosensors.

Body portion 14, includes reference electrode 28, working electrode 30, and counter electrode 29. Conductor trace 22 connects contact 16 to reference electrode 28, conductor trace 24 connects contact 18 to working electrode 30, and conductor trace 26 connects contact 20 to counter electrode 29. As discussed in examples below, each of these structures is fabricated in or on substrate 32, which is preferably a flexible layer having a thickness between about two and about ten mil (between about 50 µm and about 250 µm) of a material, such as polyimide or polyester, that is non-permeable to the analyte (s) of interest. Traces 22, 24, and 26 are preferably made of gold or carbon, but other conductive materials may also be used.

In one form of this embodiment, body portion 14 of sensor strip 10 is approximately rectangular in shape, being about 25 mm long and 450 µm wide, and is placed within a hollow fiber membrane (not shown) to enhance biocompatibility while in use. Working electrode 30 is rectangular (at least when viewed from above, as in FIG. 1), and is about 100 µm wide and 325 µm long. Working electrode 30 contains a reagent mixture suitable for the application. In one form of this embodiment, the reagent mixture comprises a conductive matrix (of carbon particles), a catalyst (manganese dioxide), an enzyme (glucose oxidase), a polymeric binder, and a solvent for the polymeric binder. This reagent mixture, on removal of the solvent, forms a porous, conductive matrix that fills, or at least substantially fills, a cavity in substrate 32 to form electrode 30. Fabrication of these structures is discussed below. In these forms, the porous reagent matrix exposes a great deal of reagent surface area for reaction, even though the planar portion of the electrode is quite small. The opening to the containment cavity regulates diffusion by the analyte into and out of the cavity, which in some embodiments provides improved control of variables in the reaction measurement, and a corresponding improvement in measurement accuracy.

When the sensor is in place, biological fluid enters the cavity containing the working electrode 30, and the glucose in the fluid reacts with the enzyme, changing the electrical impedance characteristics of the working electrode 30. A driver circuit is put in electrical communication with electrode 30 via contact 18 and trace 24, and with reference electrode 28 and counter electrode 29 via contacts 16 and 20, and traces 22 and 26, respectively. The electrical potential at one or more electrodes is controlled and the resulting current (s) is/are analyzed (or vice versa) to determine the concentration of glucose in the fluid, as is known in the art.

In various alternative embodiments, more or fewer electrodes are included on sensor strip 10, as would be understood by those skilled in the art.

The fluid is in contact with a cavity that is sized a particular way to achieve a particular result. Some of these embodiments include a containment volume ("cavity" elsewhere herein) that is approximately cylindrical in shape. In other embodiments, one end of the containment volume may be substantially wider than the other (such as a circular opening having a diameter that is twice the diameter of the circular opening at the other end), wherein analyte permeable membrane is over the smaller opening, and a co-reactant-permeable membrane is over the larger opening, so that transfer of the analyte may be controlled on one side, but sufficient co-reactant may be acquired from the fluid through the other side.

Within the cavity, reagent and in some cases a co-factor react with a component of the biological fluid from the surrounding volume. Electrical potential is created at the locus of this reaction, and must be carried to measurement circuitry to measure the concentration of analyte in the sample. In these preferred embodiments, the cavity's volume is at least about 20% (preferably at least about 50%, more preferably at least about 80%, and most preferably about 100%) filled with a porous, conductive matrix that presents reagent throughout a significant part of the cavity, and furthermore (because of the conductive nature of the matrix) carries the charge produced at the reaction locus to a conductive trace that extends into the cavity, preferably at its surrounding surface). The conductive trace extends to the surface of the substrate and on to a contact pad, which comes into electrical contact with a meter unit or other testing circuitry.

Figure 2A:
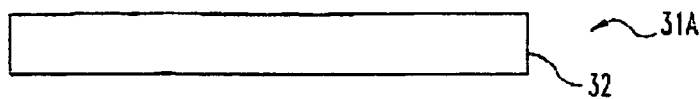
FIGS. 2A-2G are cross-sectional views of the sensor shown in FIG. 1 at various stages of fabrication, according to another embodiment of the present invention.

Turning to FIGS. 2A-2G, with continuing reference to certain structures in FIG. 1, there is shown in somewhat diagrammatic form one method of fabricating one kind of sensor according to the present invention. FIG. 2A illustrates substrate 32, which may be a substance of more or less rigidity as would occur to one skilled in the art. For example, substrate 32 may be polyimide, a ceramic material, or another material.

Figure 2B:
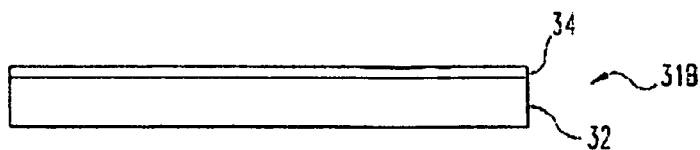
Figure 2C:
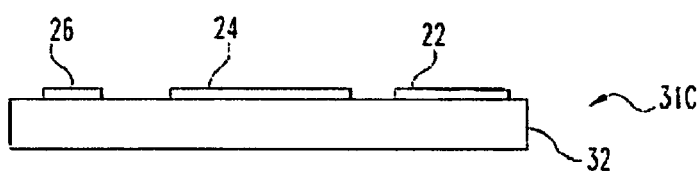

FIG. 2B shows that a layer 34 of conductive material has been deposited on substrate 32. In various embodiments, conductive layer 34 is deposited by sputtering, vapor deposition, or another method as would occur to one skilled in the art. Conductive layer 34 is then patterned, using lithographic or laser ablation techniques, for example, to define conductor traces 22, 24, and 26 on substrate 32, as shown in FIG. 2C. In other embodiments, the conductor traces 22, 24, and 26 are printed or otherwise formed onto substrate 32 using a screen printing or other patterning technique.

Figure 2D:
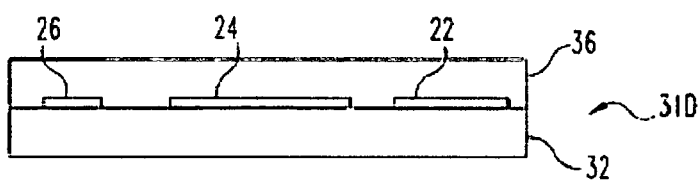

FIG. 2D shows that a layer of relatively non-conducting material 36 has been deposited over conductors 22, 24, and 26. Material 36 might, for example, be PYRALUX or VACREL, each sold by E.I. DuPont de Nemours and Company ("DuPont" herein), or the like, as would occur to one skilled in the art.

Figure 2E:
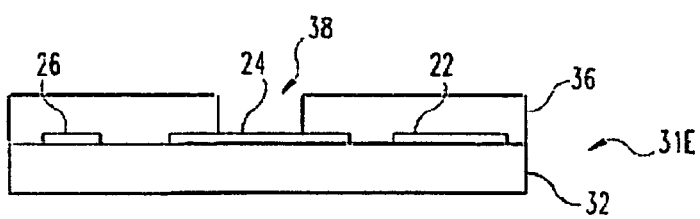
Figure 2F:
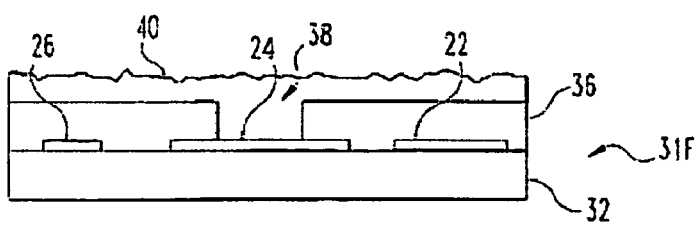
Figure 2G:
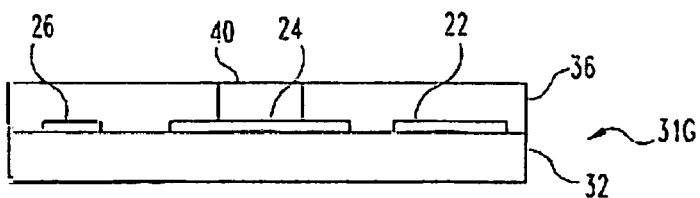

FIG. 2E shows that recess 38 has been fabricated into layer 36. Recess 38 is created, for example, by selective chemical etching, laser ablation, or other techniques. Reagent 40 is then deposited over structure 31E, including recess 38, to yield structure 31F as shown in FIG. 2F. Reagent 40 comprises a conductive matrix such as carbon particles, a catalyst such as manganese dioxide, an enzyme such as glucose oxidase, and a polymeric binder. These components are typically dispersed in an organic solvent during this depositing step. The excess (above material 36) is removed by squeegee, chemical-mechanical polishing (CMP), or similar technique, to yield structure 31G, shown in FIG. 2G. The solvent bearing reagent 40 is then evaporated away by heat or vacuum to leave the reagent 40 substantially filling recess 38. In other embodiments, reagent 40 is directly deposited into recess 38.

Figure 3A:
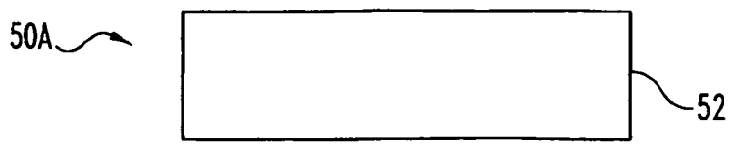
FIGS. 3A-3G are cross-sectional views of the sensor shown in FIG. 1 at various stages of fabrication, according to another embodiment of the present invention.
Figure 3B:
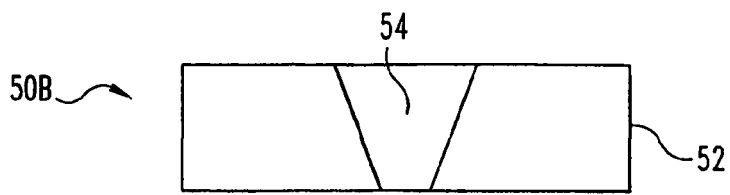
Figure 3C:
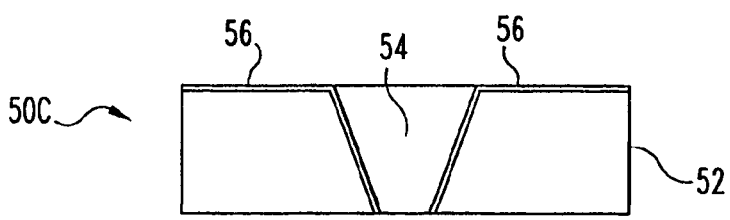

Another method of fabricating a sensor according to the present invention will now be described in relation to FIGS. 3A-3G, with continuing reference to certain structures in FIG. 1. Device 50A comprises substrate 52, made of a material that is not permeable to blood. Cavity 54, shown in FIG. 3B, is formed in substrate 52 by extraction to create device 50B. As shown in FIG. 3C, device 50C comprises the device 50B, with the addition of a conductive layer 56 that extends into recess 54 and along the top surface of device 50C.

Figure 3D:
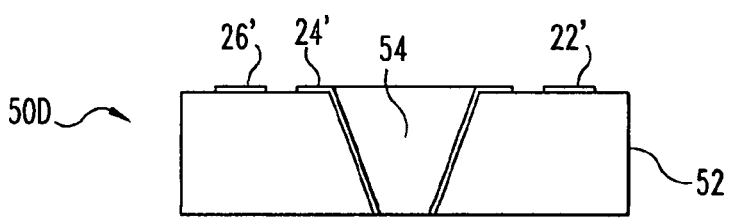
Figure 3E:
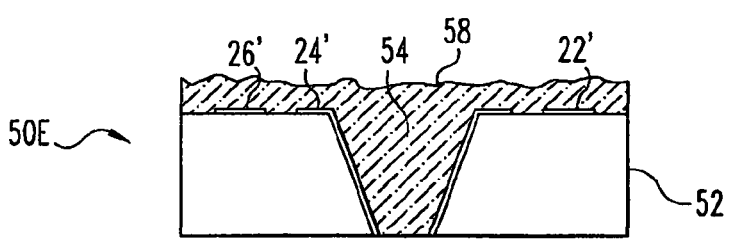

Conductor layer 56 is patterned to form device 50D, shown in FIG. 3D. Conductor traces 22', 24', and 26' correspond generally to conductors 22, 24, and 26 in FIG. 1. Reagent composition 58 is deposited on top of device 50D, at least sufficient to fill recess 54, to form device 50E, shown in FIG. 3E.

Figure 3F:
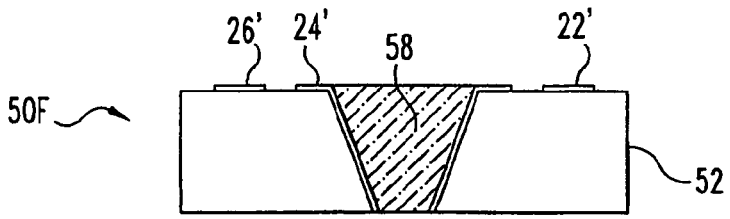
Figure 3G:
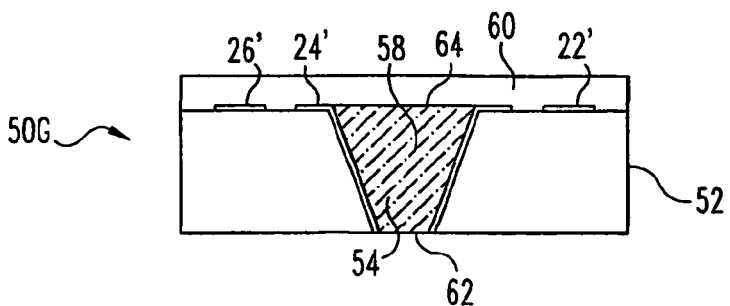

The excess reagent 58 (that above the upper surface of substrate 52) is then removed to yield device 50F as shown in FIG. 3F. This removal may, again, be performed by squeegee, CMP, or other suitable process that would occur to one skilled in the art. A layer of encapsulating material 60 is overlaid on device 50F to form device 50G, as shown in FIG. 3G. In use, bodily fluid directly contacts conductive reagent 58 at surface opening 62. Oxygen or another substance used for the detection is transported through layer 60 and into reagent 58 through surface/opening 64.

In one preferred form of this embodiment, a glucose sensor, the substrate 52 is polyimide, and the encapsulation layer 60 is silicone. The conductor layer 56 (and, therefore, conductor traces 22', 24', and 26') is gold. The reagent 58 comprises carbon particles in a porous conductive matrix that functions not only as an immobilizing and stabilizing matrix for the enzyme, but also as an active electrode element. The conductive matrix in recess 54 contacts conductor trace 24', which forms a conductive path from the working electrode to the connector area of the sensor (such as contact 18 in FIG. 1) for connection to a meter or other circuitry.

In other embodiments, the connectors are another metal, or are carbon traces printed or otherwise deposited on a surface of the substrate. In still other embodiments, the conductor is deposited around the circumference within recess 54, is deposited on one wall of recess 54, is deposited over the reagent 58, or is otherwise in contact with the electrode matrix. In various embodiments, the reagent mixture (including the conductive matrix) fills at least about 20% of recess 54, preferably at least about 80% of recess 54, and most preferably substantially all of recess 54. The remainder of recess 54 contains either air (in an unused sensor), fluid (in a sensor being used), or other material, as would occur to one skilled in the art. In yet other embodiments, recess 54 is at least half as deep as it is wide at the shortest distance across the opening 64, through which the sample enters the electrode; and preferably recess 54 is at least as deep as it is wide at the shortest distance across opening 64.

In the preferred embodiment of a glucose sensor, the catalyst in reagent 58 is preferably manganese dioxide, which reduces the required potential for hydrogen peroxide oxidation on the carbon electrode. Other suitable materials for this catalyst can be found in EP 0 603 154, which is hereby incorporated by reference. In other sensors for in vivo measurement, metallic electrodes of platinum or palladium are used to detect $H_2O_2$. With such electrodes, the potential difference required for reasonably accurate measurement is about 600-800 mV vs. Ag/AgCl, while with $MnO_2$ as the catalyst, the required potential is reduced to 300-400 mV.

The designs of many embodiments of the invention enable the efficient conversion of analyte throughout the volume in recess 54, which is efficiently electrically connected to conductor 24'. In the exemplary embodiment described above, the enzyme, glucose oxidase, is entrapped in the polymeric binder matrix and adsorbed onto the surface of the carbon particles. This solid-phase adsorption increases the stability of the enzyme and allows storage in undesiccated environments, increasing the convenience of manufacturing and storing the sensor. The hydrophobic environment of the polymeric binder matrix is also thought to increase the stability of the enzyme.

The reagent for use in a preferred embodiment of the present invention is prepared by mixing the solvent containing a polymeric binder substance with carbon particles as a pre-formulated screen printing ink mixture, with the catalyst, and any additional solvent required to produce a workable mixture. Once those components are combined, other additives are sometimes included, such as one or more detergents or hydrophilic polymers to improve the wetting characteristics, or one or more fluorocarbon polymers to improve the oxygen transport properties of the reagent. The enzyme may also be included in the reagent to produce a one-step reagent. In another variation, only the catalyst is mixed with the ink formulation, and the enzyme and other additives are added to the cured porous electrode reagent later from an aqueous solution.

The containers may be filled with the reagent mixture by dispensing the reagent mixture from a syringe needle, or by placing an excessive amount of reagent over and into the recesses, then removing the excess with a blade or squeegee. Alternatively, the reagent may be screen-printed or otherwise directly deposited into the recesses. In some cases where the recesses are formed by creating holes through the substrate, the reagent can be applied from the side of the sensor with the larger opening into the cavity (or either side, if the cavity is cylinder-shaped), the recesses being filled by capillary action through opening 64, shown in FIG. 3G. In each case, the reagent may be dried in an oven, or under vacuum, or at room temperature, depending on the requirements of the polymeric binder present in the reagent.

In further embodiments, the reagent itself may be coated with a polymeric material to resist protein adsorption and to prevent loss of enzyme over the use-lifetime of the sensor. MPC, PELLETHANE, and a plasma-produced glyme coating are examples of substances suitable for this purpose. Hydrophilic polyurethane coatings such as those described in U.S. Pat. No. 5,322,063 and U.S. Pat. No. 6,509,148 are also especially advantageous. In addition, the coating material may be designed or selected to resist interference from compounds such as ascorbic acid, uric acid, and acetaminophen. Negatively charged coatings, such as NAFION (sold by DuPont) and PVC-malonate are particularly suitable for this purpose. Alternatively, positively charged coatings, such as those discussed in EP 0 603 154, may be used. In the case of the sensor construction with holes formed all the way through the substrate, the backside of the recess, which would normally not come into contact with the sample being tested, may be coated with an impermeable material or, preferably, with a material that is permeable to any cofactor required by the reagent but not water- or analyte-permeable. A material such as a silicone polymer (for example, SYLGARD 184 from the Dow Corning Corporation) is suitable for this use when the reagent comprises an oxidase.

Alternatively or in addition, to improve the oxygen tolerance of the sensor when the reagent comprises an oxidase, a material to improve the oxygen transport may be incorporated into the reagent itself. Fluorocarbon polymers such as NAFION are suitable for this purpose.

The reference electrode 28 in various embodiments of the present invention can be any solid state reference, as will be understood by those skilled in the art. One such reference electrode material is a silver-silver chloride (Ag/AgCl) ink that is applied to a patterned gold area in a similar fashion to the reagent material discussed above. The counter electrode 29 is prepared from a carbon paste, a noble metal ink, a bare metal surface, or other material as would occur to one skilled in the art.

Once fabricated, the sensor is cut from the substrate by any of various methods known to those skilled in the art. A preferred method is a wet-etch process that creates cuts around the periphery of the sensor and leaves smooth, rounded edges. The outline of the sensor is preferably created prior to the patterning of electrodes and reagent deposition. In other embodiments, the outline may be formed at the same time as recesses for the electrodes are formed. Bridges are preferably left to retain the sensor in a fixed position relative to the substrate sheet to make subsequent processing steps easier. After fabrication, the bridges may be cut or punched, and the sensor is removed from the sheet. The sensors may then be inserted into hollow-fiber membranes to provide additional bio-compatibility and isolation of the sensor from cellular materials and large proteins that are often present in the subcutaneous environment.

In various other embodiments, recesses for the reagents are formed using lithographic techniques. Cylindrical electrode locations may be fabricated by laminating a photo-imageable coverlay such as PYRALUX or VACREL onto the patterned substrate, then exposing and developing the coverlay to form a hole (for example, having a diameter between 100 μm and 1000 μm, and being about 10-125 μm thick). Alternatively, the recesses may be etched into the polyimide substrate by a wet-etch process, or drilled by a laser, or created by other mechanical processes such as imprinting.

In still other embodiments, the recesses are filled with reagent mixture by placing excess reagent over and into the recesses, then removing the excess with a blade or squeegee as described in connection with FIGS. 2A-2G and 3A-3G above. In yet other embodiments, the reagent is dispensed or screen-printed into the recesses. In further embodiments where the recesses are formed in a polyimide substrate, the reagent is applied from the opposite side of the substrate, filling the recesses by capillary action.

Figure 4:
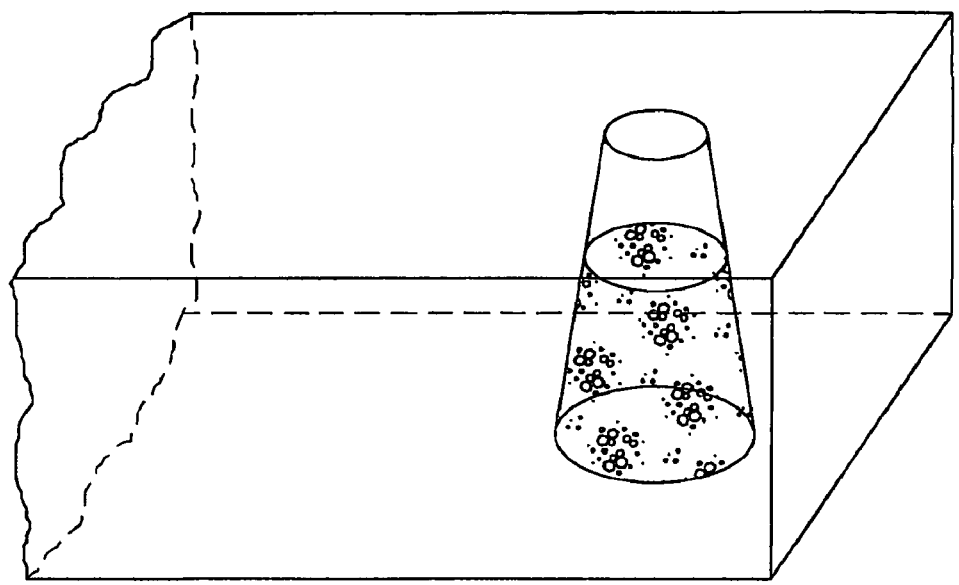
FIG. 4 is a perspective view of an end of a sensor strip according to one embodiment of the present invention.

FIG. 4 highlights an alternative cavity configuration according to another embodiment of the present invention. In this example embodiment, the cavity has the shape of a truncated cone, the top of which is a larger circle, and the bottom of which is a smaller circle. Reagent fills at least about 80% of the cavity. The sample containing the analyte enters the cavity through the smaller circle. In some variations of this embodiment, the larger circle is adjacent to a layer that is permeable to any cofactors, such as oxygen, that may participate in the reaction in the cavity. The cross-sections of the cavity, taken parallel to the smaller circle, have monotonically increasing area as they get farther from the smaller circle. Elementary geometry indicates that, for a truncated, right, circular cone (a "conical frustum"), and given smaller circle radius $r_0$, larger circle radius $r_1$, and height h, the area of the smaller circle is $A=\pi r_0^2$, and the total volume of the cavity is $$V = \frac{\pi h}{3}(r_0^2 + r_0 r_1 + r_1^2).$$

The ratio of the cavity volume to the area of the sample opening is thus $$\frac{V}{A} = \frac{h}{3}\left(1 + \frac{r_1}{r_0} + \frac{r_1^2}{r_0^2}\right).$$

It is noted that, if we define R to be the ratio $r_1/r_0$ of the larger (bottom) radius to the smaller (top) radius, then R>1 and the volume to entry-area ratio is $$\frac{V}{A} = \frac{h}{3}(1 + R + R^2) > h.$$

In some preferred embodiments, h is at least about as long as the diameter $2r_0$ of the smaller circle, so in such embodiments this V/A ratio is at least about twice the smaller (top) radius $r_0$. In other embodiments, h is at least about twice as long as the diameter $2r_0$ of the smaller circle, so in such embodiments this V/A ratio is at least about four times the smaller (top) radius $r_0$.

Figure 5:
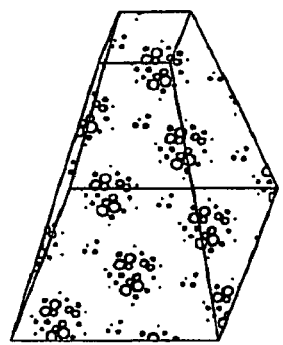
FIG. 5 is a perspective view of an alternative cavity configuration for use in the sensor of FIG. 4.

FIG. 5 shows an alternative cavity configuration according to yet another embodiment of the present invention. In this embodiment, the cavity has the shape of a truncated pyramid, the top and bottom of which are substantially square. Again, the sample enters the cavity through the smaller square opening (at the top). This cavity, for example, is substantially full of the conductive reagent matrix discussed in the embodiments shown above. Again, cross-sections of the cavity, taken parallel to the smaller square, have monotonically increasing area as they get farther from the smaller square opening. Given this truncated, right, square pyramid (a "pyramidal frustum") with small square opening side length $s_0$, large square opening side length $s_1$, and height h, the area of the small square is $A=s_0^2$, and the volume of the cavity is $$V = \frac{h}{3}(s_0^2 + s_0 s_1 + s_1^2).$$

The ratio of cavity volume to the area of the sample opening is thus $$\frac{V}{A} = \frac{h}{3}\left(1 + \frac{s_1}{s_0} + \frac{s_1^2}{s_0^2}\right).$$

Again, if R is defined to be the ratio the side length of the larger opening to the side length of the smaller opening (i.e., $s_1/s_0$), then $$\frac{V}{A} = \frac{h}{3}(1 + R + R^2) > h$$

again. In some preferred embodiments, this ratio is at least about the same as the side length $s_0$ of the smaller (top) square opening.

Figure 6:
FIG. 6 is a perspective view of another alternative cavity configuration for use in the sensor of FIG. 4.

FIG. 6 shows another alternative cavity configuration according to still another embodiment of the present invention. In this embodiment, the cavity is cylindrical and at least about 20 percent full of conductive reagent matrix. The cross-section of the cylinder is substantially the same from one end of the cavity to the other. With a cylindrical cavity of radius r according to this embodiment, the area of the sample opening is, again, $A=\pi r^2$, and the total volume of the cavity is $V=\pi r^2 h$. The ratio of the cavity volume to the area of the sample opening is thus $$\frac{V}{A} = h.$$

In some preferred embodiments, this ratio is at least about 2r, or at least about the diameter of the sample opening.

Subcutaneous sensors of the current art use membranes to cover the sensor active surface that are directly in contact with the body fluid. These membranes serve the purpose of restricting the diffusion of analyte to the sensor active surface in order to improve the sensor measurement range or linearity. They also serve to hinder access to the sensor surface of material or substances from the external fluid that might impact the sensor performance, such as by fouling the sensor active surface. These membranes generally become fouled with biological material with time, and the diffusion of analyte through them becomes restricted. In this circumstance, the sensitivity of the sensor changes, and the sensor must be recalibrated, or it will deliver inaccurate results.

Other problems with membranes may also occur. For example, the membranes may swell through absorption of the bodily fluid, increasing permeability to the analyte, or the membranes may be degraded by contact with the bodily fluid. Components in the body, such as enzymes, or cellular activity, such as from macrophages, may increase permeability to the analyte. Any change in the permeability of the membrane of such a sensor leads to inaccuracy or the need for recalibration.

Current subcutaneous sensors are made to be resistant to the effects of contact with the in vivo environment by covering them with a membrane that reduces the adhesion of protein or cellular material. These membranes are also frequently formulated to limit the diffusion of the analyte through the membrane. This diffusion limitation may be required to achieve sensitivity to that analyte over the required measurement range. These membranes cover the sensitive area of the sensor and adhere tightly to the surface to fulfill both required functions.

Subcutaneous glucose sensors, for example, typically incorporate a membrane to provide an interface to the tissue in which they are implanted. Such membranes typically allow the diffusion of glucose and other small molecules to the sensor surface, but prevent the passage of larger molecules such as proteins, and intact cells. The membranes may combine multiple functions, such as providing the biological interface, encouraging vascularization, reducing diffusion of glucose to the sensor, enhancing oxygen delivery to the sensor, etc. However, these membranes are subject to fouling, swelling, or degradation over the lifetime of the sensor, altering the rate at which glucose can diffuse to the sensor, causing a change in the effective sensitivity of the sensor and creating errors in the measurement values, or the need for recalibration.

The foregoing issues have been addressed in a variety of ways. Membranes that reduce and resist fouling to greater or lesser extents have been developed and applied. Measurement methods which are more independent of the membrane permeability have been developed. The most widely pursued alternative approach is the use of microdialysis or microperfusion to collect a liquid sample in which the analyte has equilibrated with the in vivo tissue, and to remove the sample to a sensor system for analysis. These methods remove the sensor from the subcutaneous environment. Microperfusion has the advantages of microdialysis, and claims improved resistance to membrane fouling through the use of large holes in the catheter, which cannot be blocked by protein adsorption.

However, membrane fouling and sensor drift are still significant issues with subcutaneous glucose sensors that have improved membranes and materials. Microdialysis methods have greatly increased complexity of the measurement device, and suffer from time lags due to the requirement to move liquid within the system. This also yields a very long response time for the analytical system, as the fluid must be pumped to the remote sensor at a slow rate to ensure consistent recovery of analyte from the tissue.

Some embodiments of the present invention provide a subcutaneous sensor that does not exhibit significant changes in sensitivity, leading to erroneous results or requiring recalibration. The solution of the current invention maintains the advantages of the microdialysis solution, but avoids the increased complexity.

Various forms of the present invention provides a subcutaneous sensor and associated systems and methods that provide distinct advantages over certain prior art approaches. In general, some embodiments of the present invention provide a sensor system that includes a biosensor and an encapsulating membrane that is spaced from the biosensor to provide an internal volume of fluid in contact with the biosensor. The membrane allows for desired equilibrium between the external body fluid and the internal volume of fluid, and therefore allows for accurate analyte reading by the biosensor. In various embodiments, the spacing is fixed (using spacers between the biosensor and the membrane) or variable (such as where the biosensor is not secured in a rigid spatial relationship with the membrane). In some embodiments, the distance h between the membrane and the active area might be defined as the distance between nearest points; an average distance from each point on the active surface, taken perpendicular to that surface; or the closest membrane point to the active area measured perpendicular to the surface of the active area. The size of the internal volume is preferably controlled in relation to the active area of the sensor. In preferred embodiments, given a sensor active area of s, the internal volume is at least about $s^{3/2}/10$, or $s^{3/2}$, or $10s^{3/2}$.

The sensor system is distinguished from at least some prior art in that a separate membrane is included which is spaced from the biosensor, rather than being located directly on the active area of the biosensor. This allows the surface area of the membrane to be much larger compared to the active area of the biosensor. This further provides a reservoir of fluid, i.e., the internal volume of fluid, that is in fluid communication with both the active area of the biosensor and, through the membrane, the body fluid. Moreover, the interior volume is characterized in that the diffusion coefficient of the analyte in the interior volume is about the same as, or greater than, the diffusion coefficient of the analyte in the membrane.

These forms of the invention, therefore, provide a sensor system in which the active area is removed from the interfacial membrane, and has a much smaller active area than the area of the interfacial membrane that contacts the tissue in which the sensor is implanted. Due to the large surface area of the membrane, the internal, equilibration volume maintains an analyte concentration that is very nearly identical to that of the tissue in which it is immersed, even when diffusion of analyte across the membrane is hindered or reduced. The biosensor, on the other hand, consumes small amounts of analyte due to its relatively small contact area with the equilibrium volume. Thus, the analyte concentration that the sensor measures remains very nearly identical to that in the surrounding tissue, even in the presence of hindered diffusion across the membrane surface. Further, the relatively larger area of the interfacial membrane means that it will take longer for fouling to occur, as opposed to the situation where the membrane is comparably sized to the active area of the biosensor. This yields a longer useful life for the sensor system.

Figure 7:
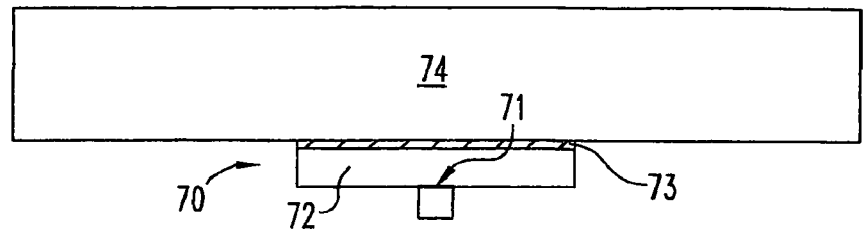
FIG. 7 is a cross-sectional view of a sensor according to another embodiment of the present invention.
Figure 9:
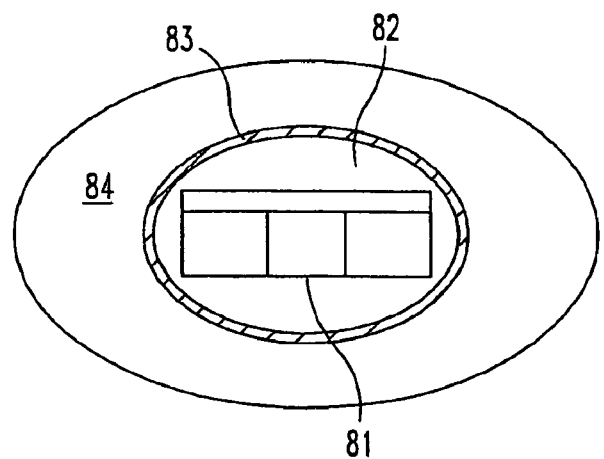
FIG. 9 is a cross-sectional view of a sensor according to the embodiment shown in FIG. 8.

It will be appreciated that the advantages of the present invention are obtained in a variety of configurations for a biosensor and encapsulating membrane. For example, in one approach the biosensor has a portion of its surface that is the active area, and the encapsulating membrane only extends over, and is spaced from, the active area of the biosensor. In another approach, the entire biosensor, including one or more inactive areas, is surrounded by the membrane. In a particularly preferred embodiment, the biosensor is received within a membrane structure that is in the form of a cylinder or other convenient shape. The sensor membrane, for example, can be planar as shown in FIG. 7, cylindrical as shown in FIG. 9, or another shape. The shape of the interior volume will be largely determined by the shape of the sensor membrane and the sensing area of the biosensor. These varieties of configurations are all intended to be encompassed herein by reference to an "encapsulating" membrane.

The present invention finds utility with a great variety of biosensors. The operative concept behind some embodiments of the invention is a sensor system having a relatively large encapsulating membrane compared to the active area of the biosensor, together with an internal volume within the membrane that is generally in equilibrium with the external fluid on the outside of the membrane, and in communication with the sensing area of the biosensor. The nature of the biosensor is therefore not critical to the operation of the present invention, and any biosensor type that alters the concentration or amount of an analyte as it operates to detect an analyte in a fluid is useful with the invention. In preferred embodiments, the biosensor is an electrochemical sensor, and a particular example of a sensor system is one in which the biosensor is useful for the detection of glucose as described above or in EP 0 603 154. It will be appreciated, however, that the scope of the present invention is not so limited, and these only represent examples of the many other biosensors and analytes with which the present invention has utility.

It is further noted that the biosensor may separately include various configurations to provide communication with the internal volume of fluid. For example, the biosensor may have an exterior surface that directly contacts the internal fluid, or it may include surface layers or membranes that further impact the diffusion of the analyte to the sensing area. As used herein, the term "sensing area" is intended to encompass such a wide variety of biosensor configurations. The sensing area is the effective area in which actual sensing, e.g., electrochemical reacting, occurs.

The choice of encapsulating membrane may similarly vary widely. Forms of the present invention are useful for a wide variety of analytes, and the membranes may accordingly be chosen to correlate to the type of analyte and type of biosensor that is employed. The membranes may combine multiple functions, such as providing the biological interface, encouraging vascularization, reducing diffusion of analyte to the sensor, enhancing oxygen delivery to the sensor, etc. Such membranes are well known in the art for use directly on the sensing area of biosensors, and by way of example, these same membranes may be used in the present invention as the encapsulating membrane. Selection of appropriate biosensors and associated membranes for use in the present invention for the detection of various analytes is therefore well within the skill in the art.

It will be appreciated that the size of the internal volume will have an impact on the sensitivity and other operating characteristics of the sensor system. It will take longer for a large interior volume to reach equilibrium when there is a change in the external body fluid, due to the lag time for analyte to diffuse through the membrane. On the other hand, a relatively larger internal volume assists in other respects, such as reducing the effect of fouling of the membrane over time.

The practical limitation on the relative dimensions of the equilibrium volume and the biosensor is the response time of the system to changes in analyte concentration in the external environment. This presents the opportunity of trading off the increase in diffusion resistance for increase in response time. For example, the lag time can be "tuned" to the desired application by selecting the shape and dimensions of the active area of the biosensor in relation to the size, position, and shape of the membrane. Proper selection of such parameters will yield more stable results, and a sensor system that can be calibrated less frequently and has a longer use lifetime.

The size of the encapsulating membrane, and therefore of the interior volume, may be selected and optimized for particular sensor systems. This will depend on the nature of the biosensor, analyte, body fluid, membrane, and other factors. The selection of parameters for such systems is within the skill in the art without undue experimentation, and further discussion herein is therefore unnecessary.

Referring to FIGS. 7-10, there are shown several alternative embodiments of a sensor system of the present invention. The system in FIG. 7 has a biosensor including Sensor Active Surface 71. This portion of the biosensor is sensitive to the analyte of interest, and for example converts the analyte into a measurable signal. Such surface may be, for example, an electrochemical enzymatic sensor. The Sensor Active Surface 71 is in fluid contact with the Sensor Interior Volume 72, and produces a signal that is related to the amount or concentration of an analyte in the Sensor Interior Volume 71. The Sensor Interior Volume 72 is separated from the External Volume 74 by the Sensor Membrane 73. The Sensor Membrane 73 separates the Sensor Interior Volume 72 from the External Volume 74. Analyte is able to penetrate the Sensor Membrane 73 to reach the Sensor Interior Volume 72. However, some components of the External Volume 74 are hindered or prevented by the Sensor Membrane 73 from entering the Sensor Interior Volume 72. The Sensor Membrane 73 may be for example a microdialysis membrane made of polyamid or polysulfone.

The area of the encapsulating membrane 73 is significantly larger than the area of the Sensor Active Surface 71, for example about 2 times, 4 times, or 10 times larger, up to about 100 times larger. As the membrane 73 begins to be fouled by material from the External Volume 74, the maximum possible rate of diffusion of analyte across the membrane 73 decreases. The amount of analyte crossing the membrane 73 is the product of the net rate per unit area and the area of the membrane 73. The small sensor consumes analyte at a rate proportional to its concentration in the Sensor Interior Volume 72 and the area of the Sensor Active Surface 71. Thus, the larger the area of the Sensor Membrane 73 relative to the Sensor Active Surface 71, the less the sensor signal will change in response to a change in the maximum rate of analyte diffusion across the membrane 73.

Described in the preceding materials are embodiments of biosensors suitable for in vivo use. It has been found that additional approaches may be useful to enhance the biocompatibility of the such sensors—both for the preceding designs and more generally. To exemplify this, the following presents a discussion of the use of a biocompatible phospholipid coating (MPC) or/and a semipermeable hollow fiber membrane. The following presents one embodiment demonstrating the configuration of an in vivo device in this manner, and it will be appreciated that modifications to these embodiments, as well as other designs of in vivo sensors, can be readily accomplished in accordance with the concepts discussed herein.

Sufficient biocompatibility is a prerequisite for use of any sensor in humans regarding safety and efficacy. To improve the biocompatibility of the sensor and to enhance the in vivo lifetime, the sensor is covered by a biocompatible phospholipid coating (MPC) or/and with a semipermeable hollow fiber membrane. Both the MPC coating and the hollow fiber membrane exclude large proteins and cells and should avoid electrode fouling processes. Moreover, the diffusion of potential toxic components into the subcutaneous space should be slowed or even avoided.

After implantation of a biosensor, the organism starts a wound healing process with different phases. Wound healing is a very complex process and is still unclear in some detailed aspects. One of these phases—the fibrous reaction (FBR)—is accompanied with an increase of more loosely or densely fibrous tissue. The fibroblasts begin to produce collagen and after several days, up to weeks, the foreign material (here, the biosensor) will be encapsulated in a collagen(ous) bag. The thickness of such a collagen(ous) bag depends on the biocompatibility of the foreign material (e.g., the biosensor). At least the diffusion time of the analyte to be measured depends on the thickness of this capsule.

One of the reasons for this tissue reaction (tissue damage, inflammation, insufficient wound healing, encapsulating with fibrous tissue, infiltration of different inflammation cells, mediators, cytokines and so on) after implantation of a biosensor into the subcutaneous space is in the case of reagent based sensors (e.g., glucose oxidase) caused by the diffusion of (cell) toxic compounds (e.g., hydrogen peroxide) within the tissue, especially around the active area 71 of the sensor.

Since an organism can serve itself with many natural defense mechanisms (e.g., redox systems, enzymes such as catalase (in the case of hydrogen peroxide)) this local tissue reaction depends on the local concentration of the toxic compounds.

With the use of the present membrane system, these compounds could react with other reactive agents in the tissue fluid within the artificial compartment between the surface 71 of the sensor and the membrane 73. Moreover, these active substances could diffuse over the entire membrane surface so that the total amount will be dispersed. So there will be no more local accumulation of the toxic compounds around the sensing surface area 71 of the sensor, and these compounds will diffuse over the entire surface of membrane 73 so that the amount-per-area is less a factor. That is, a particular rate of accumulation per unit area will affect the overall device less in a system using a membrane with a larger surface area than one using only a membrane directly adjacent to the sensor active area.

Another reason for using such a membrane system is the possibility for the analyte to diffuse over the entire membrane surface to the active area in case of partial closing of membrane pores (e.g., by cell adhesion or protein adsorption). Here, fouling of a membrane that results in the partial closing of the pores has less of an impact on sensor performance, since more membrane surface area is available for diffusion of the analyte from the external fluid volume to the internal volume, to the active area of the sensor.

Figure 8:
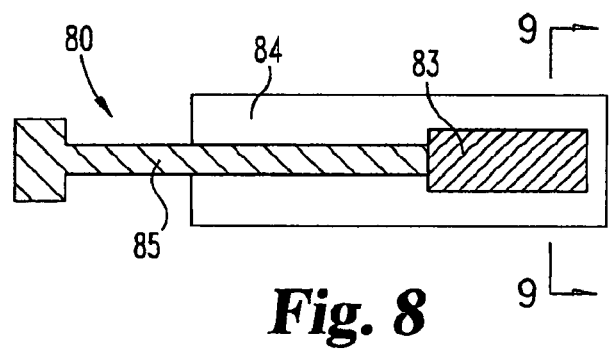
FIG. 8 is a plan view of a sensor according to still another embodiment of the present invention.

FIGS. 8 and 9 illustrate yet another in vivo sensor according to the present invention. In FIG. 8, sensor 80 includes membrane 83 around a biosensing active area. External volume 84 of fluid containing one or more analytes of interest is in contact with membrane 83, through which the analyte moves to reach the active area itself. Lead 85 extends out of membrane 83 to a control device (not shown), which operates the electrochemical sensor and acquires the output data, as will be understood by one of ordinary skill in the art without undue experimentation.

FIG. 9 shows a cross-section of sensor 80, as indicated in FIG. 8. The analyte in external volume 84 moves through membrane 83 to inner volume 82. Active area 81 of the sensor includes a reagent and electrical leads to drive and monitor the electrochemical sensing reaction. In this embodiment, membrane 83 surrounds the active sensor area 81 and the substrate that the active area 81 is in or on. This provides a very large surface area for membrane 83, with the resulting advantages discussed herein.

Figure 10:
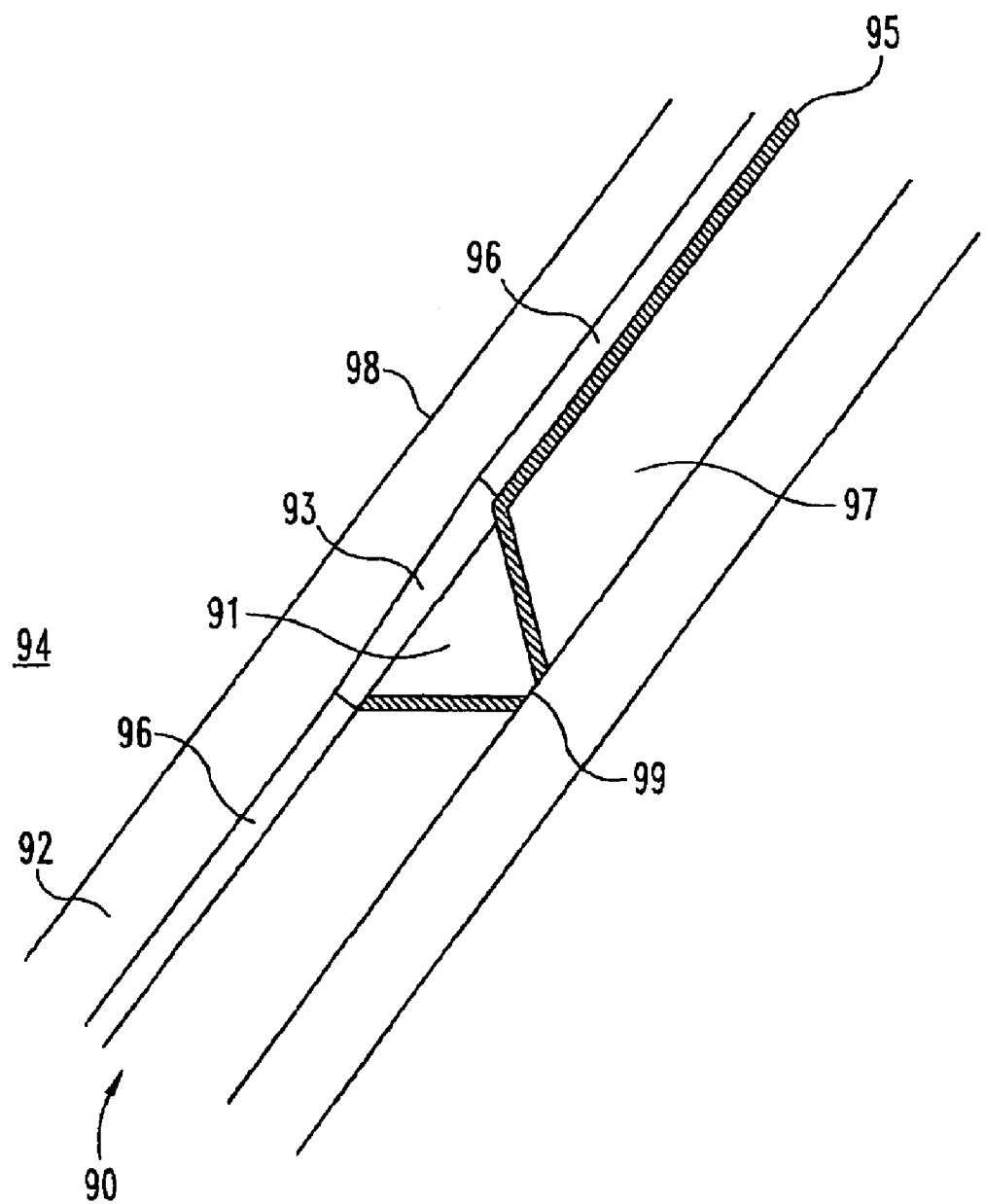
FIG. 10 is a cross-sectional view of a sensor according to yet another embodiment of the present invention.

Some embodiments of the present invention, including the embodiment shown in FIG. 10, provide a subcutaneous sensor 90 for in vivo testing of the concentration or presence of an analyte comprising a sensor head that can be implanted into the subcutaneous space 94 with a sensor active volume 91 that is sensitive for an analyte, and a membrane 98 that encapsulates at least a part of the sensor's active volume 91, whereby the membrane 98 is spaced from the surface to provide an internal volume (or internal compartment) of fluid 92 between the sensor's active volume 91 and the membrane 98 when the sensor 90 is implanted into the subcutaneous tissue. The subcutaneous sensor 90 may further comprise a chemical reagent in active volume 91, and the internal volume 92 may be filled with solution, e.g., ringer solution, for avoiding air bubbles.

The sensor membrane may be connected with the sensor head by any appropriate means, such as a biocompatible glue. The sensor in one embodiment is coated with a biocompatible polymer that is permeable for the analyte, for example MPC. The hydrophilic polyurethane coatings of U.S. Pat. No. 5,322,063 or U.S. Pat. No. 6,509,148 may also be advantageously used. The embodiment illustrated in FIG. 10 includes a conductive matrix in active volume 91 that includes a carbon paste, $MnO_2$, and GOD. Cover layer 96 protects conductive trace 95 from interaction with the fluid in inner space 92 (and protects the fluid from the conductor as well), and includes a silicone membrane 93 over one end of active volume 91. Thus, in this glucose-sensing example, glucose and oxygen enter active volume 91 through port 99, and oxygen enters through silicone membrane 93. The glucose oxidation reaction occurs in active volume 91, and generates an electrical signal on conductor 95, which electrically connects the sides of active volume 91 to the sensor output lead(s). In other sensors, different membranes, electrode structures, and component shapes may be used, as will occur to those of ordinary skill in the art without undue experimentation.

The membrane may be a semi-permeable dialysis hollow fiber, or may be made of polyamide or another material (e.g., polymer) with an appropriate cutoff (e.g., in case of glucose sensors, between 10-20 kD).

For representative embodiments, cytotoxicity was tested according to ISO 10993-5 using material itself and extracts according to ISO 10993-12, inhibition of cell growth and damage was evaluated. The absence of effects on cell growth and its morphology under working conditions (U=370 mV) of the sensor indicates appropriate fixing and caging of the electrode chemistry. The moderate cytotoxicity under non-working conditions may be caused by H2O2 generated by GOD-mediated glucose oxidation.

Histomorphological response to the working electrode (WE) without and with membranes was investigated in male Sprague Dawley rates after an implantation period of 10 days. The test material was inserted subcutaneously. The base foil of the sensor was used as control. Foreign body reaction (FBR) and vascularization were determined.

Severe FBR occurred using the sensor without any membrane. Both MPC and polyamide membranes reduced FBR. The sensor covered by both MPC and polyamide membranes resulted in a FBR comparable to controls. The results indicated biocompatibility of the sensors tested even under the worst conditions (e.g., missing $H_2O_2$ consumption in case of power failure).

These investigations demonstrate that MPC coating and covering by hollow fiber membrane is effective in avoiding cytotoxicity and in improving biocompatibility. Reduction of FBR and enhancement of neovascularization provide good sensor performance in vivo.

All publications, prior applications, and other documents cited herein are hereby incorporated by reference in their entirety as if each had been individually incorporated by reference and fully set forth herein.

While the invention has been illustrated and described in detail in the drawings and foregoing description, the same is to be considered as illustrative and not restrictive in character, it being understood that only the preferred embodiments have been shown and described and that all changes and modifications that would occur to one skilled in the relevant art are desired to be protected.

What is claimed is:

1. An electrochemical sensor, comprising:
   a substrate at least partially defining a cavity;
   an oxygen-permeable material adjacent the cavity;
   a reference electrode; and
   a working electrode substantially filling the cavity, the working electrode comprising a catalyst, a porous conducting matrix and an enzyme;
   wherein the reference electrode is electrically connectable to the working electrode through a liquid sample,
   the cavity having a smaller opening, and a larger opening having an area at least as large as that of the smaller opening, and the smaller opening being open sufficiently to allow analyte to pass into the cavity, wherein the larger opening is adjacent the oxygen-permeable material.

2. The electrochemical sensor of claim 1, wherein the smaller opening is circular.

3. The electrochemical sensor of claim 1, wherein the larger opening is circular.

4. The electrochemical sensor of claim 3, wherein the smaller opening is circular.

5. An electrochemical sensor, comprising:
   a substrate at least partially defining a cavity;

a reference electrode; and a working electrode substantially filling the cavity, the working electrode comprising a catalyst, a porous conducting matrix and an enzyme;

wherein the reference electrode is electrically connectable to the working electrode through a liquid sample and wherein the catalyst comprises manganese dioxide.

6. The electrochemical sensor of claim 5 in which the conducting matrix comprises carbon particles.

7. A strip for testing the concentration or presence of an analyte, comprising:

a first layer having a top surface and a bottom surface, a contact end and a sensing end, a first contact and a second contact at or near the contact end, a first electrode location at or near the sensing end;

a second electrode location near the first electrode location, and a cavity within and defined by the first layer at the first electrode location, the cavity having an opening through the top surface;

at least two conductors on the first layer, including a first conductor electrically connecting the cavity and the first contact, and a second conductor electrically connecting the second electrode location and the second contact;

a conductive matrix filling at least about 20% of the cavity's volume, the matrix comprising a reagent; and a reference electrode at the second electrode location, wherein the first conductor extends into the cavity to at least partially define the cavity.

8. An electrochemical sensor, comprising:

a substrate having first and second surfaces and at least partially defining a cavity extending between the first and second surfaces;

a reference electrode;

an oxygen-permeable material adjacent the cavity; and a working electrode substantially filling the cavity, the working electrode comprising a porous conducting matrix, wherein the cavity has a smaller opening and a larger opening that has an area at least as large as that of the smaller opening, the smaller opening being open at the first surface of the substrate sufficiently to allow analyte to pass into the cavity, the larger opening being adjacent the oxygen-permeable material;

wherein the reference electrode is electrically connectable to the working electrode through a liquid sample.

9. A strip for testing the concentration or presence of an analyte, comprising:

a first layer having a top surface and a bottom surface, a contact end and a sensing end, a first contact and a second contact at or near the contact end, a first electrode location at or near the sensing end;

a second electrode location near the first electrode location, and a cavity within and defined by the first layer at the first electrode location, the cavity having an opening through the top surface, the cavity being substantially surrounded, except at the opening, by one or more materials that are non-permeable by the analyte, at least one of the one or more materials being permeable to a co-reactant to the reagent;

at least two conductors on the first layer, including a first conductor electrically connecting the cavity and the first contact, and a second conductor electrically connecting the second electrode location and the second contact;

a conductive matrix filling at least about 20% of the cavity's volume, the matrix comprising a reagent; and a reference electrode at the second electrode location.

10. The strip of claim 9, wherein the conductive matrix fills at least about 80% of the cavity's volume.

11. The strip of claim 9, wherein the first conductor extends into the cavity to at least partially define the cavity.

12. The strip of claim 9, wherein the first conductor is disposed along the bottom surface of the first layer.

13. The strip of claim 9, wherein the conductive matrix fills at least about 80% of the cavity's volume.

14. The strip of claim 9, wherein the conductive matrix substantially fills the cavity.

15. The strip of claim 9, wherein at least one of the one or more materials is oxygen-permeable.

16. The strip of claim 15, wherein one or more of the at least one oxygen-permeable material has a side disposed adjacent to the bottom surface of the first layer.

17. The strip of claim 15, wherein the material that is oxygen-permeable is adjacent to the bottom surface of the first layer.

* * * * *